United States Patent [19]

Southwell

[11] Patent Number: 4,637,078
[45] Date of Patent: Jan. 20, 1987

[54] UNDERGARMENT FOR HANDICAPPED

[76] Inventor: Patricia C. Southwell, 3901 Leland St., San Diego, Calif. 92106

[21] Appl. No.: 735,130

[22] Filed: May 17, 1985

[51] Int. Cl.$^4$ ............................................. A41B 9/04
[52] U.S. Cl. .................................................... 2/408
[58] Field of Search ........................... 2/402, 405, 408

[56] References Cited

U.S. PATENT DOCUMENTS

| | | | |
|---|---|---|---|
| 1,083,712 | 1/1914 | Uyeda | 2/408 |
| 2,548,660 | 4/1951 | Feldman | 2/408 |
| 2,638,900 | 5/1953 | Gruenberg et al. | 2/408 |
| 3,207,155 | 9/1965 | Casey | 2/405 X |
| 3,496,576 | 2/1970 | Artzt | 2/405 X |
| 3,974,836 | 8/1976 | Carlson | 2/408 X |
| 4,280,230 | 7/1981 | La Fleur | 2/408 |

FOREIGN PATENT DOCUMENTS

| | | | |
|---|---|---|---|
| 1084303 | 7/1954 | France | 2/408 |
| 280164 | 4/1952 | Switzerland | 2/405 |
| 590934 | 7/1947 | United Kingdom | 2/405 |
| 678623 | 9/1952 | United Kingdom | 2/405 |

OTHER PUBLICATIONS

Resource Guide of Continence Aids and Services, 1st Edition Summer 1984, 41 pages, John R. Jeter, Jr., Illustrator.

Primary Examiner—H. Hampton Hunter
Attorney, Agent, or Firm—Baker, Maxham & Jester

[57] ABSTRACT

An undergarment for the handicapped comprises a brief or panty style garment having a lower front panel covering the crotch area that is releasably secured by hook and loop fastening means to a lower edge of the front panel of the garment for providing quick and complete access to the crotch area for catheterization and the like. Alternate embodiments include a slit in the front panel for the male version and leg straps for encircling the legs for a female embodiment.

1 Claim, 5 Drawing Figures

UNDERGARMENT FOR HANDICAPPED

BACKGROUND OF THE INVENTION

The present invention relates to undergarments for the handicapped and pertains particularly to an undergarment providing quick and easy access for catheterization.

Many handicapped individuals, particularly those who are paralyzed below the waist, often need to catheterize themselves for relief of the kidneys or the like. The traditional undergarments prevent ready access for the purpose of catheterization.

With the traditional garments for both male and female, it is difficult to gain access to the crotch area of the body for catheterization without the complete removal of the undergarment. While access openings are provided in the traditional male undergarment, such opening is not adequate for the required purpose. In addition, either complete or partial removal of the garment is traditionally difficult for the handicapped. The necessary maneuvering and the like for gaining access while wearing the traditional undergarment creates the danger that the individual may fall from his chain or other support.

Accordingly, it is desirable that improved undergarments providing easy access to catheterize oneself is desirable.

SUMMARY AND OBJECTS OF THE INVENTION

Accordingly, it is the primary object of the present invention to provide a simple and improved easy access undergarment.

In accordance with the primary aspect of the present invention, an undergarment of the traditional brief or panties type comprises a quick release lower front panel for providing easy and complete access to the crotch area of the individual.

BRIEF DESCRIPTION OF THE DRAWINGS

The above and other objects and advantages of the present invention will become apparent from the following description when read in conjunction with the drawings wherein.

DETAILED DESCRIPTION OF A PREFERRED EMBODIMENT

Figure 1:
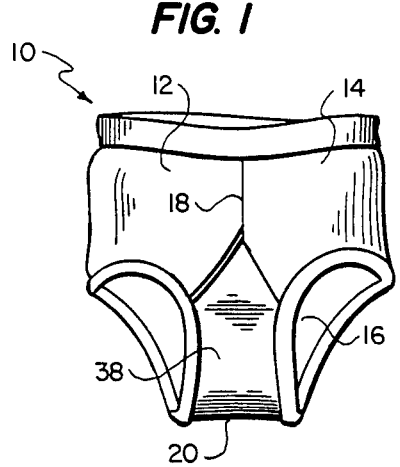
FIG. 1 is a front elevation view of a male garment in accordance with the invention.
Figure 2:
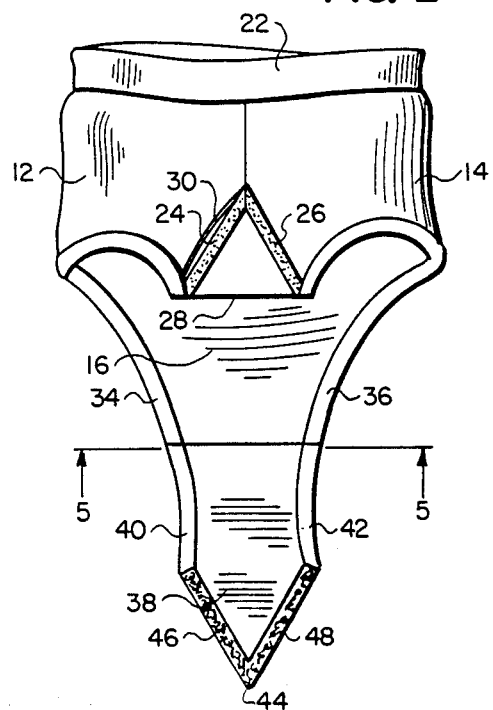
FIG. 2 is a view like FIG. 1 showing the garment open for access.

Referring to FIG. 1 of the drawing, an undergarment constructed in accordance with the present invention is illustrated and designated generally by the numeral 10. The garment is of the general style of men's briefs of the type generally referred to as Jockey style. The garment is made up of a plurality of panels of a pliable fabric material, typically of the many garment materials available, such as cottons, cotton blends, nylons and various blends of these and other fabrics. The fabric material may also be of the woven or knitted construction.

In an exemplary form of the briefs or garment, the garment is constructed of a continuous or single fabric panel cut and shaped to form a plurality of body panels comprising a front panel defined by a pair of flaps 12 and 14 extending forward and from a back panel 16 and secured along a seam 18. These panels together form a generally tubular like garment encircling the lower trunk or waist of a body with the back panel extending downward and terminating at a lower edge at an edge or seam 20 covering the buttocks.

In the illustrated embodiment, a waistband 22 is secured along the upper edge of the front and back panels with the front panels extending downward and terminating at a lower front edge which includes a generally V-shaped notch formed by lower edges 24 and 26. A generally triangular shaped panel 28 is fitted into the V-shaped notch and secured such as by stitching to the front panels and includes a band or hem like structure 30 which together with a similar structure on the lower edge 24 of panel 12 forms a slit for access to and extension of the male penis for the male garment.

The back panel extends downward and is curved along the side edges 34 and 36 with the edges hemmed and shaped in a traditional fashion to extend around the legs to form a portion of the leg opening. A lower or lower front panel 38 is secured to the lower edge 20 of the back panel and extends between the legs with side edges 40 and 42 cooperating with the edges 34 and 36 to form the leg openings. The panel 38 extends upward and overlaps the lower center portion 28 of the front panel and terminates in a V-shaped edge 44 having the generally V-configuration of the edges of panel 28. Fastening means of the hook and loop type include a pair of hook strips 46 and 48 extending along the edges of the panel 38 for engaging and hooking the fabric of the panel 28 along the edges thereof. The material of the panels in a preferred embodiment comprise a knitted fabric therefor forming the loop structure for cooperative engagement and securement by the hook strips 46 and 48.

In this embodiment during normal wear of the garment, the front panel is secured as shown in FIG. 1 to the lower portion of the front panel 12 and 14 to form a brief of the traditional style. When access is required, the edge of the front panel 38 is grasped by the fingers and pulled away to release the hook and loop fastening means and permitting the panel 38 to drop downward providing access to the crotch or genital area of the male.

Figure 3:
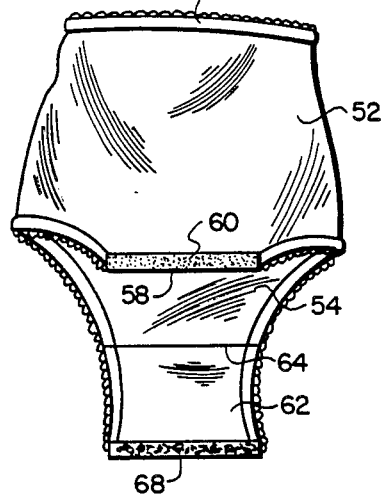
FIG. 3 is a view like FIG. 2 of an alternate embodiment.

Referring to FIG. 3, a panties or brief style embodiment of the invention designed primarily for females is illustrated and designated generally by the numeral 50. In this embodiment, a panel of fabric as previously described forms front and back panels 52 and 54 of the garment with the lower side edges of the front panel and back panels cooperating to form portions of the leg openings in a traditional manner. A waistband 56, preferably of the elastic type, extends around the top edge of the front and back panel. The front panel extends downward and terminates at the front thereof in a straight edge 58 at which may be secured loop panel portion 60 of hook and loop fastening means. A lower front panel 62 is secured at 64 to the lower edge of the back panel 54 and extends between the legs upward and has an edge or terminates in an edge 66. A hook or loop portion 68 of hook and loop fastening means extends across the edge adjacent the edge 66 of panel 62 and cooperatively engages the other hook and loop fastening means 60 at the lower edge of the front panel 52.

When the lower panel 62 is secured at its front edge to the lower edge of the panel 52, the panties have the configuration of the typical or traditional panties. When access is needed for catheterization or the like, the front panel is grasped along the edge 66 thereof, pulling the hook and loop fastening means out of engagement, permitting the flap to drop downward as shown in FIG. 3. This provides easy access for catheterization or the like.

Figure 4:
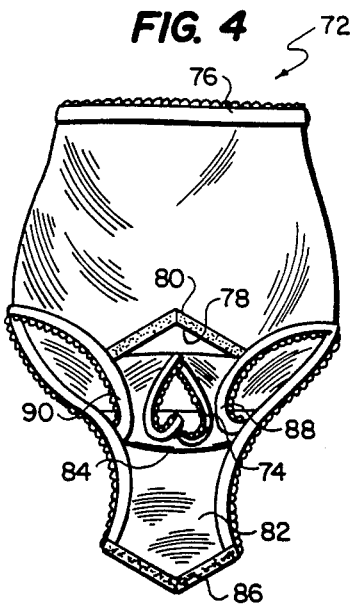
FIG. 4 is a view like FIG. 2 of another embodiment.

Referring to FIG. 4 of the drawings, an alternate embodiment of the invention designed for a female is illustrated and designated generally by the numeral 72. In this embodiment, a panel of fabric material, as in the previous embodiments, is shaped and secured together to form front and back panels, with a waistband 76 around the top edge of the two panels as in the previous embodiments.

The front panel, as in the previous embodiment, terminates at a lower edge 78 at which position a hook and loop fastening means 80 may be secured.

A lower panel 82 is secured, as in the previous embodiments, at a bottom edge of the back panel 74 extending between the legs, up and covering the crotch area, terminating in a front edge. A hook and loop strap portion means 86, designed to cooperate with loop fastening means 80 extends across the edge of the front panel.

An additional feature of this embodiment includes straps 88 and 90 which extend from the front and back panels along the sides thereof to provide means for encircling the legs forming the leg openings. This embodiment is designed particularly for small children to hold the garment in place and prevent the bottom of the undergarment from getting away from the child. An additional inner panel 84 can extend over the crotch area between the front and back panels and between the side straps 88 and 90. The panel 84 can be provided with an access opening as shown having a finished surrounding edge 74.

Figure 5:
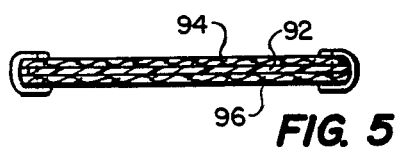
FIG. 5 is a view of a bottom panel such as would be taken generally on line 5—5 of FIG. 2.

Referring to FIG. 5, a section of the front panel or a preferred form of the front panel is illustrated wherein the panel includes a waterproof flexible sheet 92 of a suitable plastic or the like sandwiched between a pair of fabric panels 94 and 96. It is desirable in most instances that the front panel and crotch area of the garment be waterproof. This embodiment provides one form of a waterproof panel construction for any one of the briefs.

Other forms are available, such as waterproof treatment of the fabric itself. Other approaches are also possible within the scope of the invention.

The garment can also be used in conjunction with a disposable pad by the incontinent or for other personal care.

While I have illustrated and described my invention by means of specific embodiments, it is to be understood that numerous changes and modifications may be made therein without departing from the spirit and scope of the invention as defined in the appended claims.

I claim:

1. An undergarment of the panties type for the handicapped, said garment comprising:
   a plurality of panels of soft pliable fabric secured together for forming an undergarment for covering the human anatomy at the juncture of the legs with the truck, and having means defining a waist opening and a pair of leg openings, said plurality of panels comprising a front panel terminating at a lower edge above the crotch;
   first hook and loop fastening means secured to and extending along said lower edge;
   a back panel secured to said front panel for forming a tube portion for receiving the trunk and defining said waist opening;
   a releasable lower panel connected to said back panel across the crotch area and up the front and terminating at a forward edge, said lower panel having a waterproof portion for extending across the crotch area;
   second hook and loop fastening means secured to and extending along said forward edge for releasable securement to said first hook and loop fastening means at the lower edge of the front panel for covering the crotch area and for providing easy access to the crotch area of anatomy;
   a pair of straps each extending along each side of the lower edge of said front panel for defining a respective leg opening, said leg openings being substantially at the juncture of the wearer's legs and trunk in the worn position and connected at opposite ends to said back panel; and
   an additional inner panel extending over the crotch area and connected on opposite sides to said straps and at the top and bottom edges to said front and back panels respectively, said inner panel having a centrally disposed, access opening provided with a finished surrounding edge.

* * * * *